(12) United States Patent
Chiarelli et al.

(10) Patent No.: US 6,464,965 B1
(45) Date of Patent: Oct. 15, 2002

(54) SUNSCREEN COMPOSITION

(75) Inventors: Joseph A. Chiarelli, Broadview Heights, OH (US); Harinath B. Bathina, Lenexa, KS (US); Dilip Desai, Hudson; Walter Lang, Mayfield Heights, both of OH (US)

(73) Assignee: Noveon IP Holdings Corp., Cleveland, OH (US)

( * ) Notice: Subject to any disclaimer, the term of this patent is extended or adjusted under 35 U.S.C. 154(b) by 0 days.

(21) Appl. No.: 09/509,008

(22) PCT Filed: Sep. 23, 1998

(86) PCT No.: PCT/US98/19872

§ 371 (c)(1),
(2), (4) Date: May 25, 2000

(87) PCT Pub. No.: WO99/15144

PCT Pub. Date: Apr. 1, 1999

Related U.S. Application Data

(60) Provisional application No. 60/059,884, filed on Sep. 24, 1997.

(51) Int. Cl.[7] .............................. A61K 7/42; A61K 9/00; A61K 7/00
(52) U.S. Cl. .......................... 424/59; 424/400; 424/401; 514/937; 514/938
(58) Field of Search ................................ 424/400, 401, 424/59; 514/937, 938

(56) References Cited

U.S. PATENT DOCUMENTS 5,543,136 A * 8/1996 Aldous ........................ 424/59
5,545,407 A * 8/1996 Hall et al. ................... 424/401
5,725,844 A    3/1998 Gers-Barlag et al.
5,827,508 A * 10/1998 Tanner et al. ................. 424/59
5,914,101 A *  6/1999 Tapley et al. .................. 424/59
5,965,066 A * 10/1999 Koch et al. .................. 252/589

FOREIGN PATENT DOCUMENTS

| DE | 197 25 087 | 12/1998 |
| EP | 0 535 972 | 7/1993 |
| EP | 0 824 086 | 2/1998 |
| WO | WO92/17159 | 10/1992 |
| WO | WO94/04131 | 3/1994 |
| WO | WO95/12381 | 5/1995 |
| WO | WO96/41614 | 12/1996 |
| WO | WO97/17406 | 5/1997 |
| WO | WO98/13016 | 4/1998 |

OTHER PUBLICATIONS

STN, File Supplier, Karlsruhe, DE, File XP002095178, 1996.
Chemical Abstracts, vol. 127, AN=267786, & Hewitt et al.:"effective use of physical sunscreens; effect of hydrocolloids on sunscreen efficacy" Conf. Proc., 1996, pp. 63–81, Ansburg, DE.

* cited by examiner

Primary Examiner—Jose' G. Dees
Assistant Examiner—Marina Lamm
(74) Attorney, Agent, or Firm—Thoburn T. Dunlap; George W. Moxon, II

(57) ABSTRACT

Disclosed are sunscreen compositions comprising zinc oxide and at least one of an effective amount of carbomer and an effective amount of $C_{10}$ to $C_{30}$ alkyl acrylate crosspolymers. The compositions most preferably utilize an oil in water emulsion. Also disclosed are related processes for producing and using such compositions.

15 Claims, No Drawings

SUNSCREEN COMPOSITION

CROSS REFERENCE TO RELATED APPLICATION

The present application claims priority from U.S. Provisional Application Ser. No. 60/059,884, filed on Sep. 24, 1997.

BACKGROUND OF THE INVENTION

1. Field of the Invention

The present invention relates to a sunscreen composition comprising an effective amount of zinc oxide and at least one of a carbomer and $C_{10}$ to $C_{30}$ alkyl acrylate crosspolymers in a stable emulsion. The present invention also relates to associated processes for producing and using such compositions.

2. Description of Related Art

Exposure to ultraviolet radiation is a major concern as a result of its aging effects and its contribution to the formation of cancerous cells in the skin.

Organic sunscreen agents have been incorporated in a variety of cosmetic applications. As will be appreciated, the primary application of such agents is in tanning and sunscreen lotions. Formulating many personal care products such as tanning and sunscreen lotions is becoming increasingly complex as efforts are made to promote stability and efficacy of the final product. Increasingly sophisticated formulations and processing techniques significantly increase the expense faced by the manufacturer.

Furthermore, there typically exist limits on the concentration and frequency of use of many organic sunscreens. Accordingly, concerns have arisen regarding the potential for irritation resulting from organic sunscreens penetrating into a user's skin. It is also these limited use levels that have necessitated many formulators to use combinations of different types of sunscreen agents to obtain relatively high sun protection factor (SPF) products.

Physical sunscreens, mainly comprising inorganic pigments, have been utilized to increase SPF and to eliminate or reduce the high concentration levels of organic sunscreens and therefore attempt to reduce the potential for skin irritation. These inorganic pigments are also very effective in providing protecting from UVA radiation.

However, currently known sunscreen formulations comprising physical sunscreen agents or inorganic pigments, present difficult problems for formulators attempting to develop stable emulsion products. Physical sunscreens are typically difficult to maintain in a uniform suspension, in that they readily settle from the liquid carrier and often agglomerate.

One method of increasing emulsion stability has been to incorporate carbomers and $C_{10}$ to $C_{30}$ alkyl acrylate crosspolymers into suspension systems. Carbomers and $C_{10}$ to $C_{30}$ alkyl acrylate crosspolymers have been used in sunscreens and other cosmetic and personal care products for years as thickeners, stabilizers, and suspending aids.

Titanium dioxide is recognized as a successful physical sunscreen and has been used in a variety of commercially available sunscreen and skin care products. Titanium dioxide has several beneficial characteristics that make it attractive to the formulator and the end user. First, titanium dioxide is relatively inert. It is insoluble in water and dilute acid. As a result, the material will not react with other components in skin care formulations. Second, the properties of titanium dioxide are such that emulsions containing titanium dioxide are relatively stable.

Carbomers and $C_{10}$ to $C_{30}$ alkyl acrylate crosspolymers have been successfully used in sunscreen formulations containing titanium dioxide. Compatibility between these polymers and titanium dioxide is due to the fact that titanium dioxide does not dissociate in the aqueous phase. Such compatibility is also due to the fact that titanium dioxide has a negative surface charge which is compatible with the polymers which are generally anionic.

In emulsion-based formulations containing both (i) carbomers and/or $C_{10}$ to $C_{30}$ alkyl acrylate crosspolymers and (ii) titanium dioxide, the titanium dioxide may be formulated into either a nonaqueous or an aqueous phase with little concern. The only concern is that the pH of the formulation be kept above the isoelectric point so that agglomeration of the inorganic particles, i.e., titanium dioxide, does not occur.

Although sunscreen compositions based upon titanium dioxide are generally satisfactory, a need exists for an improved physical sunscreen composition, preferably one that utilizes zinc oxide. Specifically, it would be desirable to provide a sunscreen composition able to exhibit relatively high SPF values without the accompanying potential for skin irritation.

Attempts have been made to incorporate zinc oxide, an inorganic or physical sunscreen agent, into various formulations, including sunscreens. Zinc oxide provides significantly greater transparency properties with respect to visible light as compared to titanium dioxide, yet also provides protection from harmful UV radiation. However, as far as is currently known, sunscreen formulations comprising zinc oxide have met only limited success. This is believed to stem from the very reactive nature of zinc oxide and the accompanying problems of formulation instability. Accordingly, it would also be desirable to provide a sunscreen formulation, particularly one utilizing zinc oxide that is relatively stable and so has a long shelf life.

SUMMARY OF THE INVENTION

The present invention achieves the foregoing objectives and provides in a first aspect, a sunscreen composition comprising (i) an emulsion vehicle including an aqueous phase and an oil phase, (ii) zinc oxide dispersed in the oil phase, (iii) a crosslinked carboxylic acid polymer, (iv) one or more stabilizing agents incorporated in either or both of the aqueous and oil phases so that the zinc oxide is maintained, or at least substantially so, in the oil phase and substantially precluded from entering the aqueous phase, and (v) an aqueous buffering system with chelating agents to control pH and reduce the migratory tendency of zinc to interact with the carboxylic acid polymer.

In another aspect, the present invention provides a method for significantly improving the stability of a formulation, preferably a sunscreen formulation, that includes an emulsion vehicle, zinc oxide, and a crosslinked carboxylic acid polymer. The method involves maintaining, or at least substantially so, the zinc oxide in the oil phase of the emulsion vehicle.

In yet another aspect, the present invention includes a method for providing protection to an individual's skin from ultraviolet radiation by applying a composition in accordance with the present invention to a user's skin that comprises zinc oxide.

DESCRIPTION OF THE PREFERRED EMBODIMENTS

In accordance with the present invention, a preferred embodiment sunscreen composition is provided comprising an effective amount of zinc oxide and an effective amount of a crosslinked carboxylic acid polymer in a stable emulsion. Preferably, the carboxylic acid polymer is in the form of at least one of (i) one or more carbomers and (ii) $C_{10}$ to $C_{30}$ alkyl acrylate crosspolymers. The term "carbomer" as used herein refers to a polymer composed of acrylic acid monomers typically crosslinked with allyl sucrose.

The properties of zinc oxide, ZnO, or surface treated zinc oxide, are quite different than those of titanium dioxide. It is these properties that are of great interest to the formulator when attempting to incorporate zinc oxide into an oil and water emulsion that must exhibit long term stability. Zinc oxide is amphoteric in nature, and so, may function as either an acid or a base. Zinc oxide is sparingly soluble in water, i.e., about 1.60 mg/l, and solubility increases greatly with decreasing pH. As a result, dissociation will occur if zinc oxide enters the aqueous phase of the emulsion. Another consequence is that at a pH less than about 6.5, the solubility of zinc oxide begins to increase at an almost exponential rate.

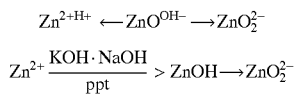

As illustrated above, upon dissociation of zinc oxide, $Zn^{2+}$ ions may react with caustic agents to form zincates. Zinc ions when in acid solution can react with sodium or potassium hydroxide to precipitate out zinc hydroxide. This typically results in a sudden pH increase, and in cases where polyacrylic acid polymers are present, crosslinking occurs between the divalent ions and the polymer. Such crosslinking results in a dramatic increase in viscosity. As will be appreciated, such viscosity increases are highly undesirable in sunscreen and other personal care formulations.

Table 1 set forth below, presents a comparison between the two inorganic pigments ZnO and $TiO_2$. It is evident why titanium dioxide, using currently known techniques. is more easily formulated and provides greater assurance of long term stability when incorporated into an oil in water system. Titanium dioxide does not react with other components of a typical emulsion even in the aqueous phase. In contrast, zinc oxide is known to dissociate and form reactive zinc ions in the aqueous phase.

TABLE 1

Comparison of Inorganic Pigments

| Zinc oxide | Titanium Dioxide |
| --- | --- |
| electropositive | electronegative |
| hydrophilic | inert in most systems |
| sparingly soluble in water and soluble in acid | Does not react with carbomer |
| Reactive with hydroxides | |
| Zinc ions complex with carbomer | |

Zinc oxide exhibits other properties which must be taken into consideration when attempting to formulate a sunscreen composition. The pH of a formulation containing zinc oxide at the isoelectric point is approximately 9. At pH levels below this point, the zinc oxide material is electropositive. Above this point, the zinc oxide material becomes electronegative. And, at the isoelectric point (IEP), the zinc oxide material has no charge and agglomeration of particles is likely.

The present inventors have discovered that if a zinc oxide material is maintained in the oil phase through adequate dispersion, then problems related to IEP, surface charge, and solubility are significantly minimized. Due to the hydrophilic nature of zinc oxide, this is not an easy task. The development of a long term stable oil phase dispersion is potentially the biggest challenge to most formulators at this time and an achievement of the present invention.

In most formulations utilizing an oil in water delivery system, there is a definite migration of zinc oxide from the oil phase into the water phase. This can significantly and adversely affect the long term stability of such systems. This is why, at this time, carbomers have provided minimal success in zinc oxide formulations where migration and dissociation may occur.

The present invention provides three classes of sunscreen compositions, each utilizing a particular type of vehicle or delivery system. A first type of composition in accordance with the present invention utilizes an oil in water emulsion. The second type of composition utilizes a water in oil emulsion. The third type of composition utilizes a complex emulsion. All of these preferred embodiment compositions utilize zinc oxide and an effective amount of one or more carboxylic acid polymers. The carboxylic acid polymer is preferably a copolymer of at least one of a carboxylic acid and a $C_{10}$ to $C_{30}$ alkyl acrylate. Preferably, the "effective amount" of the carboxylic acid polymer ranges from about 0.01% to about 2.0% (all percentages expressed herein are by weight) of the final formulation.

The amount of carboxylic acid polymer utilized in the preferred embodiment compositions varies depending upon numerous factors described herein. A typical range is from about 0.1% to about 2.0%. A preferred range of carbomer in the present invention composition is from about 0.1% to about 1.25%. A most preferred range of carbomer is from about 0.25% to about 0.75%.

Regarding the type of carbomer, nearly any grade may be employed. The present inventors have found that Carbopol® homopolymers and copolymers are acceptable for use in the present invention compositions. For example, Carbopol 907, Carbopol 941, and Carbopol ETD 2020 (a crosspolymer of acrylates and $C_{10}$ to $C_{30}$ alkyl acrylates), 2050, and 981 are preferred. The most preferred is Carbopol ETD 2050. These unique polymers stabilize difficult to emulsify systems and further should provide an added water resistance to the end product once applied to the skin. The use of these polymers can greatly increase the suspending ability and stability of the resulting formulations due to the high yield values that are characteristic of these polymers.

Regarding the $C_{10}$ to $C_{30}$ alkyl acrylate crosspolymers, there are several commercially available formulations suitable for use in the present invention. ETD™ 2020. and Pemulen™ TR-1 and TR-2 are suitable for use in the present invention compositions. The preferred $C_{10}$ to $C_{30}$ alkyl acrylate crosspolymers are ETD™ 2020, and Pemulen™ TR-1.

The typical range of use levels of the $C_{10}$ to $C_{30}$ alkyl acrylate crosspolymer is from about 0.1% to about 2.0 %. The preferred range of $C_{10}$ to $C_{30}$ alkyl acrylate crosspolymer is from about 0.1% to about 1.25% percent. A most preferred range is from 0.25% to about 0.75%.

Details of each of the preferred embodiment compositions are as follows. The first class of compositions involves incorporating zinc oxide into the oil phase of an oil in water emulsion and ensuring that migration of zinc oxide into the aqueous phase is eliminated or retarded for an extended period of time. This is accomplished by utilizing surfactants, emulsifiers, buffers, and/or chelating agents. The preparation of the dispersion is also significant in maintaining a stable emulsion. In using an oil in water delivery system, the inventors concentrated on preparing a zinc oxide in oil dispersion using surface treated and predispersed zinc oxide. Low concentration levels of low HLB (Hydrophile-Lipophile Balance) and polymeric emulsifiers were utilized, and in some cases, one or more waxes were added to help further stabilize the dispersion.

Dispersions were prepared by heating mineral oil and combinations of mineral oil and related esters, such as fatty acid esters, along with one or more emulsifiers to about 80° C. Surface treated zinc oxide was added using a typhoon mixing blade with high rpm mixing. After mixing for about 30 to about 90 minutes, a low concentration level of wax was added with cooling to help stabilize the dispersion.

Aqueous phases were made using $C_{10}$ to $C_{30}$ alkyl acrylate crosspolymers as emulsifiers, neutralized using DEA-cetyl phosphate, amino methyl propanol, or sodium hydroxide to a pH of about 6.5 to about 8.0. In some cases, a homopolymer was used and preneutralized in a similar manner. In these systems, low concentration levels of high HLB surfactant were added. Chelating agents and buffers were also added to the aqueous phase to promote stability.

In preparing the first class of compositions, the present inventors selected a low HLB surfactant or polymeric emulsifier to utilize at low concentrations so that the hydrophilic moiety of the surfactant or emulsifier would bind to exposed hydrophilic sites on the zinc oxide. As a result. the hydrophobic moiety anchors the conjugated material into the oil phase and essentially, lays over the surface of the inorganic particles. By reducing polar material in the oil phase, the inventors reduced the ease of migration to the aqueous phase. Finally, by adding a small amount of wax while cooling, additional stability was further imparted to the dispersion. By using chelating agents in the aqueous phase, zinc oxide that would otherwise migrate to the aqueous phase from the dispersion. was bound as it dissociates. Buffers were found to greatly reduce the potential for dissociation of the inorganic particles by maintaining pH, which in turn reduces or eliminates interaction with the polymer and also stabilizes the system pH.

The second class of sunscreen formulations in accordance with the present invention, utilize a water in oil emulsion delivery system. The present inventors formed invert emulsions in the presence of acrylates and $C_{10}$ to $C_{30}$ alkyl acrylate crosspolymers. Oil phase dispersions were prepared comprising zinc oxide in an oil phase consisting of mineral oil, related or fatty acid esters, sorbitan monooleate, and low concentration levels of one or more polymeric emulsifiers.

Aqueous phase dispersions of $C_{10}$ to $C_{30}$ alkyl acrylate crosspolymers were prepared and neutralized to a pH of about 7 to about 7.5. To the neutralized mucilage, the oil phase dispersion was added at room temperature with mixing. The inverts were formed almost instantly. When the $C_{10}$ to $C_{30}$ alkyl acrylate crosspolymer was removed from the formulation, emulsification would not occur.

The present inventors contemplate that the use of the present invention water in oil emulsion sunscreen formulations will promote one or more of the following in the resulting formulation: (i) improved aesthetics; (ii) increased temperature stability; (iii) reduced levels of surfactant; and (iv) limit interaction between zinc oxide and carbomer.

The third type or class of sunscreen formulations in accordance with the present invention, utilize a complex emulsion delivery system to "encapsulate" zinc oxide. In this approach, the oil phase is heated. such as to about 80° C. and the internal aqueous phase added. The resulting water in oil emulsion is allowed to cool to about 40° C. with mixing, while slowly adding the emulsion to a preneutralized, i.e., a pH of about 6.5, gel of carbomers or alkyl acrylate crosspolymers.

Initially, the present inventors attempted to disperse zinc oxide into an aqueous phase containing materials such as hydroxy propyl methyl cellulose (HPMC), Carbopol 907 (a linear polymer), and ethylenediamine tetra acetic acid (EDTA). The oil phase that was used contained a nonionic polymeric emulsifier. Once the emulsion was formed and cooled, it was added to preneutralized Pemulen polymeric emulsifier, distilled water. and EDTA. The aqueous phase was neutralized to a pH of about 6.5 to 7.0. External aqueous phases were also made using Carbopol ETD 2020 and DEA-cetyl phosphate, amino methyl propanol, and NaOH as neutralizers. All final products exhibited eventual undesirable crosslinking of the polymers and increases in pH to about 8.75.

The present inventors then attempted to disperse zinc oxide into the oil phase along with a polymeric emulsifier. The internal aqueous phase contained materials such as glycol, water, and linear polymers. Internal phase pH was adjusted to a pH of about 7.0. External phases were developed as previously described. Various formulations were made having pH values in the range of 6.5 to 8.0. All samples failed within 1 to 2 weeks.

The present inventors initially contemplated that the use of a complex emulsion would force any migrating zinc oxide into the internal phase of the emulsion, however, this was not the case. It would appear that zinc oxide has a strong affinity for the anionic carboxyl groups present in the external phase.

The inventors also contemplated that by using a neutralized zinc oxide it would be possible to disperse such into the internal phase and use the oil phase to shield the two aqueous phases. Here, it would appear that great stress was put on the complex system due again to zinc oxide's affinity for these carboxyl groups in the external phase.

From these first studies involving complex emulsions, the inventors found that by using amino methyl propanol and/or DEA-cetyl phosphate instead of the traditional hydroxide neutralizers, it was feasible to slow the reaction process between carbomers and zinc oxide. It was also discovered that surface treated zinc oxide gave significantly better results than other tested materials for complex emulsions.

Accordingly, the present invention provides a method for improving the stability of emulsions employing carboxylic acid polymers, e.g. carbomers and $C_{10}$ to $C_{30}$ alkyl acrylates, by neutralizing these polymers with amino methyl propanol and/or DEA-cetyl phosphate. Moreover, further improvements in emulsion stabilities may be realized by utilizing a surface treated zinc oxide in the oil phase of the emulsion, particularly in combination with the above noted neutralization techniques.

The present invention formulations preferably comprise a wide array of various types and grades of zinc oxide. For example, predispersed, surface treated, neutralized, or pharmaceutical grade zinc oxide may be used. A surface treated zinc oxide material appears to be easier to maintain in the hydrophobic phase of the preferred embodiment compositions than other materials evaluated, and so is generally preferred. The amount of zinc oxide employed in the sunscreen composition may range from about 1.0% to about 12.0%, preferably from about 1.0% to about 8.0%, and most preferably from about 3.0% to about 6.0%. Regardless of the particular type of emulsion utilized as a delivery system, some general guidelines are evident pertaining to the particular system used, or the selection of such a system.

Several commercially available grades of zinc oxide are suitable for use in the present invention. A dimethicone coated zinc oxide available from Sun Smart Company under the designation Zcote HP-1; and HP-1 dispersion in octyl palmitate available from Tri-K Industries have both provided significant success. Other commercially available zinc oxide formulations contemplated for use in the present invention include, but are not limited to, zinc oxide dispersed in isopropyl myrsitate available from Spectraveil Company under the designation Spectraveil IPM; zinc oxide dispersed in $C_{12}$ to $C_{15}$ alkyl benzoates also available from Spectraveil Company under the designation Spectraveil FIN; and microfine zinc oxide available from Sun Smart Company under the designation Z-cote. are all contemplated for use in the present invention. The Z-cote HP-1 zinc oxide is surfaced treated with dimethicone through a proprietary process.

It is also preferred to use particular particle sizes for the zinc oxide component. A typical range for suitable zinc oxide particles ranges from about 0.2 microns to about 100 microns. A preferred range of zinc oxide particle sizes ranges from about 0.2 microns to about 30 microns. A most preferred range of zinc oxide particle size ranges from about 0.2 microns to about 10 microns. The preferred shape for the zinc oxide particle is spherical. However, other shapes are encompassed by the present invention.

A good indicator of zinc oxide migration to the aqueous phase has been to observe pH over a period of time. As the material begins entering the aqueous phase, the pH of the system rises toward the pH of the isoelectric point. As viscosity in these systems changes, so does the rheology. As viscosity rises due to the crosslinking of the polymer by zinc ions, the rheology becomes very rubber-like and rigid. Stability at 45° C. for extended periods of time is necessary to ensure the product has a long shelf life.

Table 2, set forth below, summarizes the general characteristics of three classes of delivery systems for sunscreen formulations which include surface treated ZnO without a buffer system.

TABLE 2

|  | PH Change and time for change | Observed Viscosity Increase (Time) | Rheology change (Time) |
| --- | --- | --- | --- |
| Complex Emulsions | 7.0–8.5 24 hours | 24 hours | 24 hours |
| Oil in Water Emulsions | 6.7–10.5+ 24–48 hours | 72 hours | 72 hours |
| Water in Oil Emulsions | N/A | No change | ~3 months |

The present invention also provides several techniques by which these three types of delivery systems may be improved. By using a wax in the oil phase, increasing the mucilage pH to about 8.0 before addition of the dispersion, and by using a low concentration level of buffer, significantly improved stabilities of over one to two months have been observed. Improvements are significant if these techniques are carried out in combination.

Table 3, set forth below, illustrates the general characteristics of these three classes of delivery systems that are improved by the previously noted techniques, i.e., using a wax, increasing mucilage pH, and using a low buffer concentration.

TABLE 3

|  | PH Change (Time to equilibrate) | Observed Viscosity Increase (Time) | Rheology change (Time) |
| --- | --- | --- | --- |
| Complex Emulsions | N/A | Did not continue | — |
| Oil in Water Emulsions | 7.5–8.8 24 hours | more than 2 months | more than 2 months |
| Water in Oil Emulsions | N/A | Did not continue | — |

The previously described delivery systems, and particularly the techniques noted for improving their stability, enable a significant reduction in the interaction between carboxylic acid polymer and zinc oxide.

Examples of suitable oils for use in the present invention compositions include, but are not limited to, hydrocarbon oil, natural oil, aliphatic alcohol, fatty acid ester and silicone oil. The amount of the oil component may range from about 5% to about 95%, and preferably from about 15% to about 80%.

Examples of suitable wax for use in the present invention compositions include, but are not limited to, natural, mineral or synthetic wax. Examples of natural wax originating from animals are beeswax, spermaceti, lanolin and shellac wax, examples of natural wax originating from vegetables are carnauba wax, candelilla wax, bayberry wax and sugarcane wax. and examples of natural wax originating from minerals are ceresin wax, montan wax, paraffin wax, microcrystalline wax, Vaseline, petroleum and petrolatum wax. Examples of synthetic wax are polyol etherester such as carbowax or hydrocarbon type wax, silicone wax and polyethylene wax. Wax-type synthetic triglyceride such as ester of linear fatty acid is also useful. Most preferable examples of the wax are candelilla wax, ceresin wax, lanolin, microcrystalline wax, carnauba wax. beeswax and paraffin wax. The amount of the wax agent typically ranges from about 0.5% to about 15%, and preferably from about 1% to about 5%.

Representative examples of suitable emulsifiers for use in the present invention compositions include, but are not limited to, esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers can include, but are not limited to, polyethylene glycol 20 sorbitan monolaurate (Polysorbate 20), polyethylene glycol 5 soya sterol, Steareth-20, Ceteareth-20, PPG-2 methyl glucose ether distearate, Cetheth-10, Polysorbate 80, cetyl phosphate, potassium cetyl phosphate, diethanolamine cetyl phosphate, Polysorbate 60, glyceryl stearate, PEG-100 stearate, and mixtures thereof.

In addition, surfactants can also be used in addition to or instead of the previously noted emulsifiers. Other examples include various ethoxylated alcohols, alcohol fatty acid, polyethylene glycol triglycerides, DEA-cetyl phosphate, lecithin, and hydrogenated castor oils.

Various surfactant or emulsifiers that are commercially available may be used in the present invention formulation.

Examples of these commercially available agents include, but are not limited to various PEG-esters (Ceteth-5) available from Amerchol under the designation Solulan 5; various ethoxylated alcohols/waxes (PEG-8 Beeswax) available from Gattefosse S. A. under the designation Apifil; various alcohol fatty acids (cetyl alcohol) available from Henkel under the designation Lanette 16; various PEG-triglycerides (PEG-20 almond glycerides) available from Croda under the designation Crovol A-40; various DEA-cetyl phosphates available from Givadaun under the designation Amphisol and various hydrogenated castor oils such as available from Caschem under the designation Castorwax MP-70.

The emulsifiers can be used individually or as a mixture of two or more and comprise from about 0.1% to about 10%, more preferably from about 1% to about 7%, and most preferably from about 1% to about 5% of the compositions of the present invention.

The present invention sunscreen compositions may utilize a wide array of buffering systems such as a $Na_3PO_4.12H_2O$/Boric Acid/Citric Acid mixture for maintaining a pH of about 7.5. Conventional chelating agents and surfactants may be utilized. The amounts of these agents that are used in the composition are generally an effective amount, i.e. an amount necessary to achieve the intended function of the agent. For example, the amount of the buffer system utilized is an amount such that the buffer system is able to maintain the desired pH. The amount of the chelating agent depends upon the amount of the zinc oxide, and potential for its dissociation. The amount of surfactant is similarly governed by the characteristics of the formulation.

The compositions may further comprise one or more optional agents or components as vitamins and derivatives thereof (e.g., ascorbic acid, vitamin E, tocopheryl acetate, retinoic acid, retinol, retinoids, and the like); secondary thickening agents (e.g. polyacrylamide and $C_{13-14}$ isoparaffin and laureth-7, available as Sepigel from Seppic Corporation; polyquatemium and mineral oil, available as Salcare SC92, from Allied Colloids; crosslinked methyl quatemized dimethylaminomethacrylate and mineral oil, available as Salcare SC95 from Allied Colloids; resins; gums and thickeners such as xanthan gum, carboxymethyl cellulose, hydroxymethyl cellulose, hydroxyethyl cellulose, and magnesium aluminum silicate; cationic polymers and thickeners (e.g., cationic guar gum derivatives such as guar hydroxypropyltrimonium chloride and hydroxy propyl guar hydroxypropyltrimonium chloride, available as the Jaguar C series from Rhone-Poulenc; polymers for aiding the film-forming properties and substantivity of the composition (such as a copolymer of eicosene and vinyl pyrrolidone, an example of which is available from GAF Chemical Corporation as Ganex® V-220); preservatives for maintaining the antimicrobial integrity of the compositions; skin penetration aids such as DMSO, 1-dodecylazacycloheptan-2-one (available as Azone from the Upjohn Co.) and the like; anti-acne medicaments (resorcinol, salicylic acid, erythromycin, benzoyl peroxide, zinc, and the like); artificial tanning agents such as dihydroxyacetone and the like; skin bleaching (or lightening) agents including but not limited to hydroquinone, kojic acid and sodium metabisulfite; antioxidants; chelators and sequestrants; and aesthetic components such as fragrances, colorings, essential oils, skin sensates, astringents, skin soothing agents, skin healing agents and the like, nonlimiting examples of these aesthetic components include panthenol and derivatives (e.g. ethyl panthenol), pantothenic acid and its derivatives, clove oil, menthol, camphor, eucalyptus oil, eugenol, menthyl lactate, witch hazel distillate, allantoin, bisabalol, dipotassium glycyrrhizinate and the like.

The present invention provides a particularly preferred formulation. The most preferred formulation is set forth below in Table 4.

TABLE 4

| | Parts by Weight |
|---|---|
| Part A | |
| Oil Phase: | |
| a) Caprylic/Capric Triglycerides | 5.00 |
| b) Octyl Methoxycinnimate | 7.00 |
| c) Polyglyceryl-3-Beeswax | 1.50 |
| d) ZnO (HP-1) | 5.00 |
| Part B | |
| Aqueous Phase: | |
| e) Distilled Water | 49.00 |
| f) Disodium EDTA (Ethylenediamine tetra acetic acid) | 0.10 |
| g) Carbopol ETD 2020 polymer (Acrylates/$C_{10}$ to $C_{30}$ Alkyl Acrylates Crosspolymer) | 0.75 |
| h) Propylene glycol | 8.00 |
| i) Amphisol (Diethanolamine-cetyl phosphate mixture) | 1.50 |
| j) Amp. 95 (Amino methyl propanol) | 0.50 |
| k) pH 7.5 buffer ($Na_3PO_4.12H_2O$/Boric Acid/Citric Acid Mixture) | 20.00 |

The aqueous phase is prepared by mixing ingredients e)–g) at room temperature for about 20 minutes. Next, ingredients h) and i) are added and mixed for 10 to 15 minutes. Then, ingredient j) is added to achieve a pH of about 7 to 7.5, and ingredient k) is added last. The oil phase is then added to the aqueous phase under slow agitation, the oil phase resembling a near paste. Mixing is preferably performed at 500 rpm or less for about 10 minutes.

The sunscreen compositions of the present invention are used by application to a user's skin. As will be appreciated, the composition, if in lotion form, is typically applied onto the portions of skin expected to be exposed to, or in fact exposed to, the sun or other source of ultraviolet radiation.

While the invention has been described in detail and with reference to specific embodiments thereof, it will be apparent to one skilled in the art that various changes and modifications can be made therein without departing from the spirit and scope thereof.

What we claim is:

1. A sunscreen composition comprising:
   an oil in water emulsion including an aqueous phase and an oil phase;
   zinc oxide dispersed in said oil phase;
   an effective amount of a crosslinked carboxylic acid polymer in said aqueous phase; and
   a buffering system and at least one stabilizing agent selected from the group consisting of surfactants, emulsifiers, chelating agents, and combinations thereof in said aqueous phase whereby the pH of the aqueous phase is maintained in the range of 7.5 to 8.8 and whereby said zinc oxide is maintained in said oil phase and precluded from entering said aqueous phase.

2. The sunscreen composition of claim 1 wherein said zinc oxide is surface treated.

3. The sunscreen composition of claim 1 wherein said oil phase comprises:

zinc oxide;

mineral oil;

fatty acid esters;

sorbitan monooleate; and polymeric emulsifiers.

4. The sunscreen composition of claim 1 wherein said aqueous phase comprises $C_{10}$ to $C_{30}$ alkyl acrylate crosspolymer as said crosslinked carboxylic acid polymer.

5. The sunscreen composition of claim 1 wherein said crosslinked carboxylic acid polymer has been preneutralized with at least one of amino methyl propanol and DEA-cetyl phosphate.

6. The sunscreen composition of claim 1 wherein said crosslinked carboxylic acid polymer has been preneutralized with an agent selected from the group consisting of amino methyl propanol, DEA-cetyl phosphate, and combinations thereof.

7. The sunscreen composition of claim 1 wherein said oil phase comprises a wax.

8. The sunscreen composition of claim 1 wherein said aqueous phase is buffered to a pH value of about 8.0.

9. A method for improving the stability of an oil in water emulsion having an aqueous phase and an oil phase, and zinc oxide dispersed in said oil phase, said method comprising:

maintaining said zinc oxide in said oil phase by adding a crosslinked carboxylic acid polymer to said aqueous phase and a buffering system and at least one stabilizing agent selected from the group consisting of surfactants, emulsifiers, chelating agents, and combinations thereof to maintain the pH of the aqueous phase in the range of 7.5 to 8.8.

10. The method of claim 9 wherein said maintaining step is achieved by selecting at least one of a carbomer and a $C_{10}$ to $C_{30}$ alkyl acrylate crosspolymer for use as said crosslinked carboxylic acid polymer.

11. The method of claim 9 wherein said zinc oxide is a surface treated zinc oxide.

12. The method of claim 10 wherein said crosslinked carboxylic acid polymer is preneutralized with an agent selected from the group consisting of amino methyl propanol, DEA-cetyl phosphate, and combinations thereof.

13. The method of claim 9 wherein said maintaining step is achieved, at least partly, by increasing the pH value of said aqueous phase to about 8.0 prior to combining said aqueous phase with said oil phase.

14. The method of claim 9 wherein said formulation is a sunscreen composition.

15. A method of providing protection to an individual's skin from ultraviolet radiation, said method comprising:

applying a composition to said skin, said composition comprising an oil in water emulsion including an aqueous phase and an oil phase, zinc oxide dispersed in said oil phase, said aqueous phase having a crosslinked carboxylic acid polymer and a buffering system and at least one stabilizing agent selected from the group consisting of surfactants, emulsifiers, chelating agents, and combinations thereof in said aqueous phase, whereby said zinc oxide is maintained in said oil phase and precluded from entering said aqueous phase prior to application of said composition to said skin.

* * * * *